(12) United States Patent
Luan et al.

(10) Patent No.: US 10,653,588 B2
(45) Date of Patent: May 19, 2020

(54) COMPOSITION FOR PROTECTING THE KERATIN MATERIALS FROM SUN

(71) Applicant: L'OREAL, Paris (FR)

(72) Inventors: Tu Luan, Shanghai (CN); Yan Wang, Shanghai (CN)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/366,839

(22) Filed: Mar. 27, 2019

(65) Prior Publication Data

US 2019/0216692 A1    Jul. 18, 2019

Related U.S. Application Data

(63) Continuation of application No. 15/313,989, filed as application No. PCT/CN2014/079678 on Jun. 11, 2014, now abandoned.

(51) Int. Cl.

| | | |
|---|---|---|
| *A61K 8/02* | (2006.01) | |
| *A61Q 17/04* | (2006.01) | |
| *A61K 8/19* | (2006.01) | |
| *A61K 8/26* | (2006.01) | |
| *A61K 8/29* | (2006.01) | |
| *A61K 8/44* | (2006.01) | |
| *A61Q 5/00* | (2006.01) | |
| *A61K 8/64* | (2006.01) | |

(Continued)

(52) U.S. Cl.
CPC .......... *A61K 8/0279* (2013.01); *A61K 8/0254* (2013.01); *A61K 8/19* (2013.01); *A61K 8/20* (2013.01); *A61K 8/26* (2013.01); *A61K 8/29* (2013.01); *A61K 8/37* (2013.01); *A61K 8/375* (2013.01); *A61K 8/42* (2013.01); *A61K 8/44* (2013.01); *A61K 8/498* (2013.01); *A61K 8/64* (2013.01); *A61K 8/678* (2013.01); *A61K 8/73* (2013.01); *A61K 8/8152* (2013.01); *A61K 8/891* (2013.01); *A61K 8/894* (2013.01); *A61K 8/9794* (2017.08); *A61Q 5/00* (2013.01); *A61Q 17/04* (2013.01); *A61K 2800/412* (2013.01); *A61K 2800/43* (2013.01); *A61K 2800/621* (2013.01); *A61K 2800/622* (2013.01); *A61K 2800/651* (2013.01)

(58) Field of Classification Search
CPC .......... A61K 8/0279; A61K 8/19; A61K 8/26; A61K 8/29; A61K 8/44; A61K 8/64; A61K 8/678; A61K 8/0254; A61K 8/9794; A61K 8/20; A61K 8/37; A61K 8/375; A61K 8/42; A61K 8/498; A61K 8/73; A61K 8/8152; A61K 8/891; A61K 8/894; A61K 2800/412; A61K 2800/622; A61K 2800/651; A61K 2800/43; A61K 2800/621; A61Q 17/04
See application file for complete search history.

(56) References Cited

U.S. PATENT DOCUMENTS

| | | |
|---|---|---|
| 6,384,104 B1 | 5/2002 | Chang et al. |
| 2005/0196347 A1 | 9/2005 | Berillouet et al. |

(Continued)

FOREIGN PATENT DOCUMENTS

| | | |
|---|---|---|
| CA | 2 296 625 A1 | 7/2001 |
| EP | 1 092 421 A2 | 4/2001 |

(Continued)

OTHER PUBLICATIONS

International Search Report and Written Opinion dated Mar. 2, 2015 in PCT/CN2014/079678 filed Jun. 11, 2014.

(Continued)

*Primary Examiner* — Sean M Basquill
(74) *Attorney, Agent, or Firm* — Oblon, McClelland, Maier & Neustadt, L.L.P.

(57) ABSTRACT

The present invention relates to a cosmetic composition comprising: a) at least one UV filter; b) at least one composite particle in spherical form, having a mean size of between 0.1 and 30 μm comprising at least one particulate UV-screening agent and a core constituted of at least one inorganic material and/or of at least one organic material; c) at least one anti-oxidation active ingredient chosen from I) a compound according to formula (I) wherein each X independently represents —OPO$_3$Y, wherein Y is selected from hydrogen, Li, Na and K; II) a dimer peptide according to formula (II); III) a tocopherol or its derivatives; and IV) a mixture thereof.

18 Claims, No Drawings

(51) Int. Cl.
- *A61K 8/67* (2006.01)
- *A61K 8/9794* (2017.01)
- *A61K 8/20* (2006.01)
- *A61K 8/37* (2006.01)
- *A61K 8/42* (2006.01)
- *A61K 8/49* (2006.01)
- *A61K 8/73* (2006.01)
- *A61K 8/81* (2006.01)
- *A61K 8/891* (2006.01)
- *A61K 8/894* (2006.01)

(56) References Cited

U.S. PATENT DOCUMENTS

| | | |
|---|---|---|
| 2008/0070993 A1 | 3/2008 | Borbely |
| 2008/0233060 A1 | 9/2008 | Grune |
| 2012/0015016 A1 | 1/2012 | Galdi et al. |

FOREIGN PATENT DOCUMENTS

| | | |
|---|---|---|
| EP | 1 537 854 A1 | 6/2005 |
| EP | 2 201 928 A2 | 6/2010 |
| WO | WO 2010/118415 A1 | 10/2010 |
| WO | WO 2010/0118415 A1 | 10/2010 |
| WO | WO 2011/016143 A1 | 2/2011 |
| WO | WO 2012/104161 A1 | 8/2012 |
| WO | WO 2012/110303 A1 | 8/2012 |
| WO | WO 2014/010099 A1 | 1/2014 |
| WO | WO-2014010101 A1 * | 1/2014 ............ A61Q 17/04 |

OTHER PUBLICATIONS

Extended European Search Report dated Oct. 5, 2017 in Patent Application No. 14894490.3.

\* cited by examiner

COMPOSITION FOR PROTECTING THE KERATIN MATERIALS FROM SUN

CROSS REFERENCE TO RELATED APPLICATIONS

This Application is a continuation application of prior U.S. application Ser. No. 15/313,989, filed Nov. 25, 2016, the disclosure of which is incorporated herein by reference in its entirety. U.S. application Ser. No. 15/313,989 is the National stage of PCT/CN2014/079678, filed Jun. 11, 2014, the disclosure of which is incorporated herein by reference in its entirety.

FIELD OF THE INVENTION

The present invention relates to a composition that is capable of protecting the keratin materials from hazardous effect caused by sun. More particularly, the present invention relates to a composition comprising UV filter(s), SPF booster(s) and/or composite particle(s) in spherical form, and anti-oxidation active ingredient(s). The present invention also relates to the method of preparing a composition as such, and use thereof for protecting the keratin materials from UV radiation and pro-oxidation.

BACKGROUND OF THE INVENTION

Keratin materials, such as the skin, the scalp, and the hair, are continuously exposed to many hazardous environmental agents, including UV radiation, air pollutants, such as ozone and ionizing radiation, which generate Reactive Oxygen Species (ROS), among which, the exposure to the sun has caused to the keratin materials many hazardous problems, such as sunburn and aging caused by UV rays and pro-oxidants.

UVB rays, with a short wavelength and highly energy-intensive, are responsible for sunburns of the skin. UVA rays are less energy-intensive, but 20 times more numerous than UVB rays. The UV radiation can induce photoaging of the keratin materials, such as the skin, the scalp, and the hair.

Besides, the skin, the scalp and the hair are directly and frequently exposed to environmental pro-oxidants caused by the sun exposure and are particularly sensitive to the action of oxidative stress, its outermost lay serves as a barrier to oxidative damage that may occur. In most circumstances, the oxidizing agent is generally neutralized after reaction with keratin materials, but the reaction products formed may be responsible for cell and tissue damage. The stratum corneum, the skin barrier is the site of contact between air and skin tissue and structure biphasic lipid/protein is a crucial determinant of the barrier function of the skin. These elements can react with oxidants and be altered, which will help scaling phenomena.

Thus, the harmful effects of UV lights and peroxidation on the keratin materials affect cellular respiration of these keratin materials and result in accelerated aging of the skin with a dull complexion and premature formation of wrinkles and fine lines, as well as a decrease in the strength of the hair also take a dull appearance. In addition, because of the UV and the peroxidation, skin and hair gets dirty faster. In addition, the UV and the peroxidation can cause irritation and allergic phenomena and inflammation on the skin.

To fight against the UV rays and the pro-oxidants, various compositions comprising UV filters and/or anti-oxidation compounds were described. However, there still remains a need for a novel composition for protecting the keratin materials from hazardous effects caused by sun exposure, which possess desired sun protection factor (SPF) value, and an improved anti-oxidation effect, and stable over time.

SUMMARY OF THE INVENTION

According to one aspect of the present invention, there is provided a composition comprising:
a) at least one UV filter;
b) at least one SPF booster chosen from hollow particles, and/or at least one composite particle in spherical form, having a mean size of between 0.1 and 30 μm comprising at least one particulate UV-screening agent and a core constituted of at least one inorganic material and/or of at least one organic material; and
c) at least one anti-oxidation active ingredient chosen from
 I) a compound of formula (I)

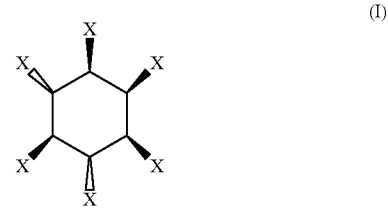

wherein,
each X independently represents —OPO$_3$Y;
Y is selected from hydrogen, Li, Na and K;
II) a dimer peptide of formula (II):

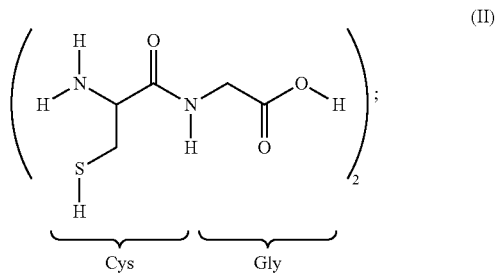

III) a tocopherol or its derivatives; and
IV) a mixture thereof.

According to another aspect of the present invention, there is provided a method for preparing a composition according to the present invention comprising mixing at least one UV filter, at least one SPF booster and/or at least one composite particle in spherical form, and at least one anti-oxidation active ingredient as described above.

According to another aspect of the present invention, there is provided a method for protecting the keratin materials, such as the skin, the scalp, and the hair, in particular, the skin, from UV radiation and pro-oxidation comprising application of the composition according to the present invention to the keratin materials.

According to one aspect of the present invention, there is provided use of a combination of at least one UV filter, at least one SPF booster and/or at least one composite particle in spherical form, and at least one anti-oxidation active ingredient in producing a composition as described above.

The composition according to the present invention can be used to protecting the keratin materials, especially the skin, the scalp and the hair, from UV radiation and pro-oxidation. The composition has an improved sun protection factor (SPF) value, and an improved anti-oxidation effect, and is stable over time.

Advantageously, the composition of the present invention can be used as a makeup composition, such as foundation, BB cream, or makeup base. It possesses light sensory and perfect makeup coverage when the composition contains additionally fillers and/or pigments.

DETAILED DESCRIPTION OF THE INVENTION

The inventors of the present invention surprisingly found that with the combination of an UV filter, a SPF booster and/or at least one composite particle in spherical form, and an anti-oxidation active ingredient, the composition according to the present invention has an improved effect on UV protection and an improved anti-oxidation effect.

According to one aspect of the present invention, there is provided a composition comprising:
 a) at least one UV filter;
 b) at least one SPF booster chosen from hollow particles, and/or at least one composite particle in spherical form, having a mean size of between 0.1 and 30 μm comprising at least one particulate UV-screening agent and a core constituted of at least one inorganic material and/or of at least one organic material; and
 c) at least one anti-oxidation active ingredient chosen from
  I) a compound of formula (I)

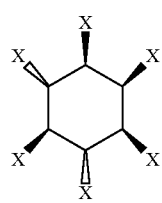

(I)

wherein each X independently represents —OPO$_3$Y, wherein Y is selected from hydrogen, Li, Na and K;
 II) a dimer peptide of formula (II):

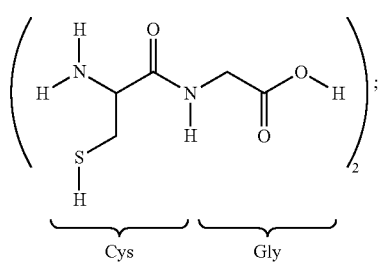

(II)

III) tocopherol or its derivatives; and
 IV) a mixture thereof.

The composition is preferably a cosmetic composition, more particularly a makeup composition.

The composition is for topical application.

The composition according to the present application may comprise at least one polysaccharide.

Preferably, the composition according to the present application may comprise at least one pigment.

The composition according to the present application may comprise at least one inorganic salt, for example selected from sodium, potassium, magnesium chloride and sulfate.

The term "mean size of the particles" in this invention is understood to mean the parameter D [4,3] measured using a "Mastersizer 2000" particle size analyser (Malvern). The light intensity scattered by the particles as a function of the angle at which they are lit is converted to size distribution accordingly to Mie theory. The parameter D [4,3] is measured; this is the mean diameter of the sphere having the same volume as the particle. For a spherical particle, reference will often be made to the "mean diameter".

The term "mean elementary size" means the size of non-aggregated particles.

The term "keratin materials" means the skin (body, face, area around the eyes), hair, eyelashes, eyebrows, body hair, nails, lips or mucous membranes.

UV Filter

The composition of the present invention comprises at least one UV filter.

There is no limitation to the type of the UV filter. Two or more types of UV filters may be used in the composition of the invention. Thus, a single type of UV filter or a combination of different types of UV filters may be used.

The UV filter can be selected from inorganic UV filters, organic UV filters, and mixtures thereof.

Organic UV Filter

The composition according to the present invention may comprise an organic UV filter.

The organic UV filter used for the present invention may be active in the UV-A and/or UV-B region. The organic UV filter may be hydrophilic and/or lipophilic.

The organic UV filter may be solid or liquid. The terms "solid" and "liquid" mean solid and liquid, respectively, at 25° C. under 1 atm.

The organic UV filter can be selected from the group consisting of anthranilic compounds; dibenzoylmethane compounds; cinnamic compounds; salicylic compounds; camphor compounds; benzophenone compounds; β,β-diphenylacrylate compounds; triazine compounds; benzotriazole compounds; benzalmalonate compounds; benzimidazole compounds; imidazoline compounds; bis-benzoazolyl compounds; p-aminobenzoic acid (PABA) compounds; methylenebis(hydroxyphenylbenzotriazole) compounds; benzoxazole compounds; screening polymers and screening silicones; dimers derived from α-alkylstyrene; 4,4-diarylbutadienes compounds; guaiazulene and derivatives thereof; rutin and derivatives thereof; flavonoids; bioflavonoids; oryzanol and derivatives thereof; quinic acid and derivatives thereof; phenols; retinol; cysteine; aromatic amino acids; peptides having an aromatic amino acid residue; and mixtures thereof.

Mention may be made, as examples of the organic UV filter(s), of those denoted below under their INCI names, and mixtures thereof.

Anthranilic compounds: Menthyl anthranilate, marketed under the trademark "Neo Heliopan MA" by Haarmann and Reimer.
 Dibenzoylmethane compounds: Butyl methoxydibenzoylmethane, marketed in particular under the trademark "Parsol 1789" by Hoffmann-La Roche; and isopropyl dibenzoylmethane.

Cinnamic compounds: Ethylhexyl methoxycinnamate, marketed in particular under the trademark "Parsol MCX" by DSM Nutritional Products; isopropyl methoxycinnamate; isopropoxy methoxycinnamate; isoamyl methoxycinnamate, marketed under the trademark "Neo Heliopan E 1000" by Haarmann and Reimer; cinoxate (2-ethoxyethyl-4-methoxy cinnamate); DEA methoxycinnamate; diisopropyl methylcinnamate; and glyceryl ethylhexanoate dimethoxycinnamate.

Salicylic compounds: Homosalate (homomentyl salicylate), marketed under the trademark "Eusolex HMS" by Rona/EM Industries; ethylhexyl salicylate, marketed under the trademark "Neo Heliopan OS" by Haarmann and Reimer; glycol salicylate; butyloctyl salicylate; phenyl salicylate; dipropyleneglycol salicylate, marketed under the trademark "Dipsal" by Scher; and TEA salicylate, marketed under the trademark "Neo Heliopan TS" by Haarmann and Reimer.

Camphor compounds, in particular, benzylidenecamphor derivatives: 3-benzylidene camphor, manufactured under the trademark "Mexoryl SD" by Chimex; 4-methylbenzylidene camphor, marketed under the trademark "Eusolex 6300" by Merck; benzylidene camphor sulfonic acid, manufactured under the trademark "Mexoryl SL" by Chimex; camphor benzalkonium methosulfate, manufactured under the trademark "Mexoryl SO" by Chimex; terephthalylidene dicamphor sulfonic acid, manufactured under the trademark "Mexoryl SX" by Chimex; and polyacrylamidomethyl benzylidene camphor, manufactured under the trademark "Mexoryl SW" by Chimex.

Benzophenone compounds: Benzophenone-1 (2,4-dihydroxybenzophenone), marketed under the trademark "Uvinul 400" by BASF; benzophenone-2 (Tetrahydroxybenzophenone), marketed under the trademark "Uvinul D50" by BASF; Benzophenone-3 (2-hydroxy-4-methoxybenzophenone) or oxybenzone, marketed under the trademark "Uvinul M40" by BASF; benzophenone-4 (hydroxymethoxy benzophonene sulfonic acid), marketed under the trademark "Uvinul MS40" by BASF; benzophenone-5 (Sodium hydroxymethoxy benzophenone Sulfonate); benzophenone-6 (dihydroxy dimethoxy benzophenone); marketed under the trademark "Helisorb 11" by Norquay; benzophenone-8, marketed under the trademark "Spectra-Sorb UV-24" by American Cyanamid; benzophenone-9 (Disodium dihydroxy dimethoxy benzophenonedisulfonate), marketed under the trademark "Uvinul DS-49" by BASF; and benzophenone-12, and n-hexyl 2-(4-diethylamino-2-hydroxybenzoyl)benzoate (UVINUL A+ by BASF).

β,β-Diphenylacrylate compounds: Octocrylene, marketed in particular under the trademark "Uvinul N539" by BASF; and Etocrylene, marketed in particular under the trademark "Uvinul N35" by BASF.

Triazine compounds: Diethylhexyl butamido triazone, marketed under the trademark "Uvasorb HEB" by Sigma 3V; 2,4,6-tris(dineopentyl 4'-aminobenzalmalonate)-s-triazine, bis-ethylhexyloxyphenol methoxyphenyl triazine marketed under the trademark «TINOSORB S» by CIBA GEIGY, and ethylhexyl triazone marketed under the trademark «UVINUL T150» by BASF.

Benzotriazole compounds, in particular, phenylbenzotriazole derivatives: 2-(2H-benzotriazole-2-yl)-6-dodecyl-4-methylpheno, branched and linear; and those described in U.S. Pat. No. 5,240,975.

Benzalmalonate compounds: Dineopentyl 4'-methoxybenzalmalonate, and polyorganosiloxane comprising benzalmalonate functional groups, such as polysilicone-15, marketed under the trademark "Parsol SLX" by Hoffmann-LaRoche.

Benzimidazole compounds, in particular, phenylbenzimidazole derivatives: Phenylbenzimidazole sulfonic acid, marketed in particular under the trademark "Eusolex 232" by Merck, and disodium phenyl dibenzimidazole tetrasulfonate, marketed under the trademark "Neo Heliopan AP" by Haarmann and Reimer.

Imidazoline compounds: Ethylhexyl dimethoxybenzylidene dioxoimidazoline propionate.

Bis-benzoazolyl compounds: The derivatives as described in EP-669,323 and U.S. Pat. No. 2,463,264.

Para-aminobenzoic acid compounds: PABA (p-aminobenzoic acid), ethyl PABA, Ethyl dihydroxypropyl PABA, pentyl dimethyl PABA, ethylhexyl dimethyl PABA, marketed in particular under the trademark "Escalol 507" by ISP, glyceryl PABA, and PEG-25 PABA, marketed under the trademark "Uvinul P25" by BASF.

Methylene bis-(hydroxyphenylbenzotriazol) compounds, such as 2,2'-methylenebis[6-(2H-benzotriazol-2-yl)-4-methyl-phenol] marketed in the solid form under the trademark "Mixxim BB/200" by Fairmount Chemical, 2,2'-methylenebis[6-(2H-benzotriazol-2-yl)-4-(1,1,3,3-tetramethylbutyl)phenol] marketed in the micronized form in aqueous dispersion under the trademark "Tinosorb M" by BASF, or under the trademark "Mixxim BB/100" by Fairmount Chemical, and the derivatives as described in U.S. Pat. Nos. 5,237,071 and 5,166,355, GB-2,303,549, DE-197,26,184, and EP-893,119, and Drometrizole trisiloxane, marketed under the trademark "Silatrizole" by Rhodia Chimie or- "Mexoryl XL" by L'Oreal, as represented below.

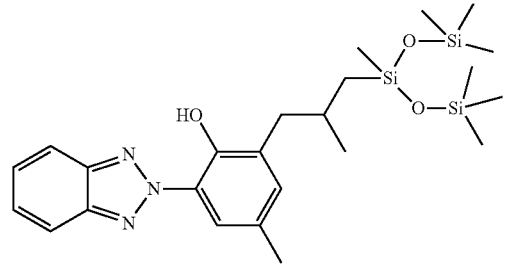 [SMILES: Cc1cc(CC(C)C[Si](C)(O[Si](C)(C)C)O[Si](C)(C)C)c(O)c(-n2nc3ccccc3n2)c1]

Benzoxazole compounds:
2,4-bis[5-1(dimethylpropyl)benzoxazol-2-yl-(4-phenyl)imino]-6-(2-ethylhexyl)imino-1,3,5-triazine, marketed under the trademark of Uvasorb K2A by Sigma 3V.

Screening polymers and screening silicones: The silicones described in WO 93/04665.

Dimers derived from α-alkylstyrene: The dimers described in DE-19855649.

4,4-Diarylbutadiene compounds:
1,1-dicarboxy(2,2'-dimethylpropyl)-4,4-diphenylbutadiene.

It is preferable that the organic UV filter(s) be selected from the group consisting of:

butyl methoxydibenzoylmethane, ethylhexyl methoxycinnamate, homosalate, ethylhexyl salicylate, octocrylene, phenylbenzimidazole sulfonic acid, benzophenone-3, benzophenone-4, benzophenone-5, n-hexyl 2-(4-diethylamino-2-hydroxybenzoyl) benzoate,
1,1'-(1,4-piperazinediyl)bis[1-[2-[4-(diethylamino)-2-hydroxybenzoyl]phenyl]-methanone 4-methylbenzylidene camphor, terephthalylidene dicamphor sulfonic acid, disodium phenyl dibenzimidazole tetrasulfonate, ethylhexyl triazone, bis-ethylhexyloxyphenol methoxyphenyl triazine, diethylhexyl butamido triazone, 2,4,6-tris(dineopentyl 4'-aminobenzalmalonate)-s-triazine, 2,4,6-tris(diisobutyl 4'-aminobenzalmalonate)-s-triazine, 2,4-bis-(n-butyl 4'-aminobenzalmalonate)-6-[(3-{1,3,3,3-tetramethyl-1-[(trimethylsilyloxy]-disiloxanyl}propyl)amino]-s-triazine, 2,4,6-tris-(di-phenyl)-triazine, 2,4,6-tris-(ter-phenyl)-triazine, methylene bis-benzotriazolyl tetramethylbutyl phenol, drometrizole trisiloxane, polysilicone-15, dineopentyl 4'-methoxybenzalmalonate, 1,1-dicarboxy(2,2'-dimethylpropyl)-4,4-diphenylbutadiene, 2,4-bis[5-1 (dimethylpropyl)benzoxazol-2-yl-(4-phenyl)imino]-6-(2-ethylhexyl) imino-1,3,5-triazine, camphor benzylkonium methosulfate, and mixtures thereof.

If presents, the organic UV filter is present in the composition of the invention in an amount of generally from 0.5% to 20%, preferably from 1% to 10% and more preferably from 3% to 7.5% by weight, relative to the total weight of the composition.

Inorganic UV Filter

The composition according to the present invention may comprise an inorganic UV filter.

The inorganic UV filter used for the present invention may be active in the UV-A and/or UV-B region.

The inorganic UV filter is generally chosen from metal oxides, preferably titanium, zinc or iron oxides, or mixtures thereof, and more particularly from titanium dioxide (amorphous or crystalline in rutile and/or anatase form), zinc oxide and mixtures thereof. Particularly preferably, the inorganic UV-screening agent is $TiO_2$.

These metal oxides may be in the form of particles, having a mean elementary size generally of less than 200 nm. Advantageously, the metal oxide particles used have a mean elementary size of less than or equal to 0.15 µm.

These metal oxides may also be in the form of layers, preferably multilayers with a mean thickness generally of less than 0.2 µm.

The inorganic UV filters in accordance with the invention preferably have a mean elementary particle size of greater than 5 nm and less than 200 nm. According to one particularly preferred embodiment of the invention, this size preferably ranges from 10 nm to 150 nm.

According to one embodiment of the invention, the inorganic UV filters may be titanium oxide-based nanopigments.

The inorganic UV filters may be coated or uncoated.

The coated inorganic UV filters are pigments that have undergone one or more surface treatments of chemical, electronic, mechanochemical and/or mechanical nature with compounds as described, for example, in Cosmetics & Toiletries, February 1990, Vol. 105, pp. 53-64, such as amino acids, beeswax, fatty acids, fatty alcohols, anionic surfactants, lecithins, sodium, potassium, zinc, iron or aluminium salts of fatty acids, metal alkoxides (titanium or aluminium alkoxides), polyethylene, silicones, proteins (collagen, elastin), alkanolamines, silicon oxides, metal oxides or sodium hexametaphosphate.

Preferably, the inorganic UV filters may be chosen from coated or uncoated Titanium dioxide.

The coated pigments are more particularly titanium oxides that have been coated:

with silica, such as the product Sunveil from the company Ikeda, with silica and iron oxide, such as the product Sunveil F from the company Ikeda, with silica and alumina, such as the products Microtitanium Dioxide MT 500 SA and Microtitanium Dioxide MT 100 SA from the company Tayca and Tioveil from the company Tioxide, with alumina, such as the products Tipaque TTO-55 (B) and Tipaque TTO-55 (A) from the company Ishihara and UVT 14/4 from the company Kemira, with alumina and aluminium stearate, such as the products Microtitanium Dioxide MT 100 TV, MT 100 TX, MT 100 Z and MT-01 from the company Tayca, the products Solaveil CT-10 W and Solaveil CT 100 from the company Uniqema and the product Eusolex T-AVO from the company Merck, with silica, alumina and alginic acid, such as the product MT-100 AQ from the company Tayca, with alumina and aluminium laurate, such as the product Microtitanium Dioxide MT 100 S from the company Tayca, with iron oxide and iron stearate, such as the product Microtitanium Dioxide MT 100 F from the company Tayca, with zinc oxide and zinc stearate, such as the product BR 351 from the company Tayca, with silica and alumina and treated with a silicone, such as the products Microtitanium Dioxide MT 600 SAS, Microtitanium Dioxide MT 500 SAS or Microtitanium Dioxide MT 100 SAS from the company Tayca, with silica, alumina and aluminium stearate and treated with a silicone, such as the product STT-30-DS from the company Titan Kogyo, with silica and treated with a silicone, such as the product UV-Titan X 195 from the company Kemira, with alumina and treated with a silicone, such as the products Tipaque TTO-55 (S) from the company Ishihara or UV Titan M 262 from the company Kemira, with triethanolamine, such as the product STT-65-S from the company Titan Kogyo, with stearic acid, such as the product Tipaque TTO-55 (C) from the company Ishihara, with sodium hexametaphosphate, such as the product Microtitanium Dioxide MT 150 W from the company Tayca.

$TiO_2$ treated with octyltrimethylsilane, sold under the trade name T 805 by the company Degussa Silices, $TiO_2$ treated with a polydimethylsiloxane, sold under the trade name 70250 Cardre UF $TiO_2Si_3$ by the company Cardre, anatase/rutile $TiO_2$ treated with a polydimethylhydrogenosiloxane, sold under the trade name Microtitanium Dioxide USP Grade Hydrophobic by the company Color Techniques.

The uncoated titanium oxide pigments are sold, for example, by the company Tayca under the trade names Microtitanium Dioxide MT 500 B or Microtitanium Dioxide MT 600 B, by the company Degussa under the name P 25, by the company Wackherr under the name Transparent titanium oxide PW, by the company Miyoshi Kasei under the name UFTR, by the company Tomen under the name ITS and by the company Tioxide under the name Tioveil AQ.

According to the invention, titanium dioxide coated with alumina and aluminium stearate, such as the products Microtitanium Dioxide MT 100 TV, is preferred.

If presents, the inorganic UV filter is present in the composition of the invention in an amount of generally from 0.01% to 10%, preferably from 0.05% to 5% and more preferably from 0.1% to 3% by weight, relative to the total weight of the composition.

SPF Booster

The high performance organic UV filter is extensively used in cosmetic products, but the drawback of using organic UV filter is also obvious, an oily, sticky and uncomfortable feeling is generally confronted. In order to achieve a high UV protection but without extensive use of organic UV filter, an effective SPF booster is designed to be used in the cosmetic composition according to the present invention.

The composition of the present invention comprises one or more SPF booster.

The term "SPF booster" means a compound or composition that, when used in a formulation in conjunction with a UV screening agent, increases the SPF value of the formulation without increasing the amount of the UV screening agent in the formulation.

The SPF booster may be selected from hollow particles, in particular hollow latex particles.

Hollow Latex Particles

"Latex" means polymer particles in the form of an aqueous dispersion which is generally stabilized with at least one emulsifier.

The hollow latex particles according to the invention have a particle size which ranges generally from 100 to 380 nm and preferably from 150 to 375 nm and more preferably from 190 to 350 nm and more particularly from 251 to 325 nm, the particle size being measured by a Brookhaven BI-90 photon correlation spectrometer.

For a given particle size, the latex particles according to the invention must in general possess a maximum hollow fraction. The latex particles preferably contain a void fraction of 0.1% to 50% and more preferably of 5% to 50%. The void fractions are determined by comparing the volume occupied by the latex particles after having been compacted from a diluted dispersion in a centrifuge, relative to the volume of non-void particles in the same composition.

The hollow latex particles according to the invention may be obtained from particles comprising at least one polymer for the core and at least one polymer for the shell. The core polymer and the shell polymer may be obtained from a single polymerization step or from a sequence of polymerization steps.

The hollow latex particles according to the invention may be prepared by the conventional techniques of emulsion polymerization. Such processes are described especially in U.S. Pat. Nos. 4,427,836, 4,469,825, 4,594,363, 4,677,003, 4,920,160 and 4,970,241 or by the conventional techniques of polymerization that are described in the following patents and patent applications: EP267726, EP331421, U.S. Pat. Nos. 490,229 and 5,157,084.

The monomers used for the shell of the latex particles are preferably constituted of one or more unsaturated nonionic ethylenic units. Optionally one or more monoethylenically unsaturated monomers containing at least one carboxylic acid group may be polymerized in the shell.

The monomers constituting the shell are selected such that they exhibit a glass transition temperature (Tg) which is sufficiently high to withstand the void of the hollow latex particle. Preferably the glass transition temperature is greater than 50° C., more preferably greater than 60° C. and more preferably still greater than 70° C. This temperature Tg may be determined by DSC (differential scanning calorimetry).

The monomers used in the emulsion polymerization in the core polymer of the latex particles of the invention are preferably constituted of one or more monoethylenically unsaturated monomers containing at least one carboxylic acid group. Preferably the core comprises at least 5% by weight of monoethylenically unsaturated monomer containing at least one carboxylic acid group, relative to the total weight of the core monomers.

The core polymer may for example be obtained by emulsion homopolymerization of the monoethylenically unsaturated monomer containing at least one acid group or by copolymerization of two or three monoethylenically unsaturated monomers containing at least one acid group. Preferably the monoethylenically unsaturated monomer containing at least one acid group is copolymerized with one or more ethylenically unsaturated nonionic monomers.

The core polymer or the shell polymer may contain from 0.1% to 20% by weight, preferably from 0.1% to 3% by weight, of polyethylenically unsaturated monomers such as ethylene glycol di(meth)acrylate, allyl (meth)acrylate, 1,3-butanediol di(meth)acrylate, diethylene glycol di(meth)acrylate, trimethylolpropane tri(meth)acrylate or divinylbenzene, relative to the total weight of core monomers. Alternatively the core polymer or the shell polymer may optionally contain from 0.1% to 60% by weight of butadiene, relative to the total weight of core monomers.

The monoethylenically unsaturated monomers containing at least one carboxylic acid group include, for example: acrylic acid, methacrylic acid, acryloyloxypropionic acid, (meth)acryloyloxypropionic acid, itaconic acid, aconitic acid, maleic acid or maleic anhydride, fumaric acid, crotonic acid, monomethyl maleate, monomethyl fumarate and monomethyl itaconate.

Use will be made more particularly of a monomer selected from acrylic acid and methacrylic acid.

The monoethylenically unsaturated nonionic monomers include, for example: styrene, vinyltoluene, vinyl acetate, vinyl chloride, vinylidene chloride, acrylonitrile, (meth)acrylamide, $C_1$-$C_{20}$ alkyl esters of (meth)acrylic acid and ($C_3$-$C_{20}$) alkenyl esters of (meth)acrylic acid, such as methyl (meth)acrylate, ethyl (meth)acrylate, butyl (meth)acrylate, 2-ethylhexyl (meth)acrylate, benzyl (meth)acrylate, lauryl (meth)acrylate, oleyl (meth)acrylate, palmityl (meth)acrylate and stearyl (meth)acrylate.

According to the invention, the term (meth)acrylic will denote the general expression encompassing both methacrylic or acrylic. The term (meth)acrylate will denote the general expression encompassing both methacrylate or acrylate.

The void part of the core of the latex particles is preferably produced by swelling the core with a swelling agent comprising one or more volatile compounds. The agent penetrates the shell in order to swell the core. The volatile components of the swelling agent may be subsequently removed by drying the latex particles, thus creating a void within the said particles. The agent is preferably an aqueous base. Mention may be made, for example, of ammonia, ammonium hydroxide, alkali metal hydroxides such as sodium hydroxide and volatile amines such as trimethylamine or triethylamine.

The hollow latex particles may be introduced into the composition of the invention with the swelling agent. In that case the volatile compounds are removed when the composition is dried. The hollow latex particles may also be added to the composition after the volatile compounds of the swelling agent have been removed.

The hollow latex particles which can be used according to the invention are those described in U.S. Pat. No. 5,663,213 and patent application EP1092421.

According to one particular embodiment of the invention the hollow latex particles used will be those constituted of a copolymer of styrene and (meth)acrylic acid or one of its $C_1$-$C_{20}$ alkyl esters under the INCI name Styrene/Acrylates Copolymer, such as the product sold under the trade name Sunspheres Powder by the company Rohm & Haas, which is an aqueous dispersion containing 86% of Styrene/Acrylates Copolymer in a mixture of 11% of PEG-8 Laurate, 2.5% of water and 0.5% of Sodium Dodecylbenzenesulfonate.

The amount of SPF booster in the compositions of the invention preferably ranges from 0.1% to 10% by weight, more preferably from 0.5% to 8% by weight, even more preferably from 0.5% to 4%, in particular from 1% to 3% by weight relative to the total weight of the composition.

Composite Particles in Spherical Form

The composite particles in spherical form used according to the invention have a mean size of between 0.1 and 30 μm, preferably between 0.1 and 20 μm and even more preferentially between 0.1 and 10 μm.

The term "spherical" means that the particle has a sphericity index, i.e. the ratio between its largest diameter and its smallest diameter, of less than 1.2.

The composite particles in spherical form used according to the present invention comprise at least one particulate UV-screening agent and a core constituted of at least one inorganic material and/or of at least one organic material.

According to a first variant, the composite particles in spherical form contain a core comprising at least one organic material and/or at least one inorganic material, in which are included particles of particulate UV-screening agent. According to this embodiment, the matrix exhibits inclusions, and particles of particulate UV-screening agent are placed in the inclusions of the matrix.

According to a second variant, the composite particles in spherical form contain a core made of an organic material and/or an inorganic material, covered with at least one layer of particulate UV-screening agent which may be connected to the matrix by means of a binder.

According to a third variant, the composite particles in spherical form contain a particulate UV-screening agent covered with at least one layer of an organic material and/or of an inorganic material.

The core may also be formed from one or more organic materials and/or inorganic materials. It may then be a continuous phase of materials such as an alloy, i.e. a continuous phase in which the materials can no longer be dissociable, or a discontinuous phase of materials, for example constituted of an organic or inorganic material covered with a layer of another different organic or inorganic material.

The weight content of particulate UV-screening agent in the composite particles in spherical form of the invention is preferably between 1% and 90%, preferably between 2% and 80% and even better still between 3% and 70%.

The organic materials that may be used to form the core of the composite particles in spherical form are chosen from the group formed by poly(meth)acrylates, polyamides, silicones, polyurethanes, polyethylenes, polypropylenes, polystyrenes, polycaprolactams, polysaccharides, polytetrafluoroethylenes, polypeptides, polyvinyl derivatives, waxes, polyesters and polyethers, and mixtures thereof.

Preferably, the matrix of the composite particles in spherical form contains a material or a mixture of materials chosen from:
  $SiO_2$,
  poly(methyl methacylate),
  copolymers of styrene and of a $C_1$/$C_5$ alkyl (meth)acrylate derivative,
  polyamides, such as Nylon®,
  polytetrafluoroethylenes.

More preferably the matrix or the core of the composite particles in spherical form comprises poly(methyl methacylate).

Particulate UV-Screening Agents

The particulate UV-screening agents according to the invention are chosen from particulate organic UV-screening agents and inorganic screening agents.

Preferably, the particulate UV-screening agents according to the invention are chosen from inorganic screening agents.

Inorganic Screening Agents

The inorganic UV-screening agent is generally chosen from metal oxides, preferably titanium, zinc or iron oxides, or mixtures thereof, and more particularly from titanium dioxide (amorphous or crystalline in rutile and/or anatase form), zinc oxide and mixtures thereof. Particularly preferably, the inorganic UV-screening agent is $TiO_2$.

These metal oxides may be in the form of particles, having a mean elementary size generally of less than 200 nm. Advantageously, the metal oxide particles used have a mean elementary size of less than or equal to 0.15 μm.

These metal oxides may also be in the form of layers, preferably multilayers with a mean thickness generally of less than 0.2 μm.

The inorganic UV-screening agents in accordance with the invention preferably have a mean elementary particle size of greater than 5 nm and less than 200 nm.

According to one particularly preferred embodiment of the invention, this size preferably ranges from 10 nm to 150 nm.

According to one embodiment of the invention, the inorganic UV-screening agents may be titanium oxide-based nanopigments.

The inorganic UV-screening agents may be coated or uncoated.

The coated inorganic UV-screening agents are pigments that have undergone one or more surface treatments of chemical, electronic, mechanochemical and/or mechanical nature with compounds as described, for example, in Cosmetics & Toiletries, February 1990, Vol. 105, pp. 53-64, such as amino acids, beeswax, fatty acids, fatty alcohols, anionic surfactants, lecithins, sodium, potassium, zinc, iron or aluminium salts of fatty acids, metal alkoxides (titanium or aluminium alkoxides), polyethylene, silicones, proteins (collagen, elastin), alkanolamines, silicon oxides, metal oxides or sodium hexametaphosphate.

As is known, silicones are organosilicon polymers or oligomers of linear or cyclic, branched or crosslinked structure, of variable molecular weight, obtained by polymerization and/or polycondensation of suitably functionalized silanes, and are essentially constituted of a repetition of main units in which the silicon atoms are linked together via oxygen atoms (siloxane bond), optionally substituted hydrocarbon-based radicals being directly attached to said silicon atoms via a carbon atom.

The term "silicones" also encompasses the silanes required for their preparation, in particular alkylsilanes.

The silicones used for coating the pigments that are suitable for the present invention are preferably chosen from the group containing alkylsilanes, polydialkylsiloxanes and polyalkylhydrogenosiloxanes. Even more preferentially, the silicones are chosen from the group containing octyltrimethylsilane, polydimethylsiloxanes and polymethylhydrogenosiloxanes.

Of course, before being treated with silicones, the metal oxide pigments may have been treated with other surface agents, in particular with cerium oxide, alumina, silica, aluminium compounds or silicon compounds, or mixtures thereof.

The coated pigments are more particularly titanium oxides that have been coated:

with silica, such as the product Sunveil from the company Ikeda, with silica and iron oxide, such as the product Sunveil F from the company Ikeda, with silica and alumina, such as the products Microtitanium Dioxide MT 500 SA and Microtitanium Dioxide MT 100 SA from the company Tayca and Tioveil from the company Tioxide, with alumina, such as the products Tipaque TTO-55 (B) and Tipaque TTO-55 (A) from the company Ishihara and UVT 14/4 from the company Kemira, with alumina and aluminium stearate, such as the products Microtitanium Dioxide MT 100 T, MT 100 TX, MT 100 Z and MT-01 from the company Tayca, the products Solaveil CT-10 W and Solaveil CT 100 from the company Uniqema and the product Eusolex T-AVO from the company Merck, with silica, alumina and alginic acid, such as the product MT-100 AQ from the company Tayca, with alumina and aluminium laurate, such as the product Microtitanium Dioxide MT 100 S from the company Tayca, with iron oxide and iron stearate, such as the product Microtitanium Dioxide MT 100 F from the company Tayca, with zinc oxide and zinc stearate, such as the product BR 351 from the company Tayca, with silica and alumina and treated with a silicone, such as the products Microtitanium Dioxide MT 600 SAS, Microtitanium Dioxide MT 500 SAS or Microtitanium Dioxide MT 100 SAS from the company Tayca, with silica, alumina and aluminium stearate and treated with a silicone, such as the product STT-30-DS from the company Titan Kogyo, with silica and treated with a silicone, such as the product UV-Titan X 195 from the company Kemira, with alumina and treated with a silicone, such as the products Tipaque TTO-55 (S) from the company Ishihara or UV Titan M 262 from the company Kemira, with triethanolamine, such as the product STT-65-S from the company Titan Kogyo, with stearic acid, such as the product Tipaque TTO-55 (C) from the company Ishihara, with sodium hexametaphosphate, such as the product Microtitanium Dioxide MT 150 W from the company Tayca.

$TiO_2$ treated with octyltrimethylsilane, sold under the trade name T 805 by the company Degussa Silices, $TiO_2$ treated with a polydimethylsiloxane, sold under the trade name 70250 Cardre UF TiO2SI3 by the company Cardre, anatase/rutile $TiO_2$ treated with a polydimethylhydrogenosiloxane, sold under the trade name Microtitanium Dioxide USP Grade Hydrophobic by the company Color Techniques.

The uncoated titanium oxide pigments are sold, for example, by the company Tayca under the trade names Microtitanium Dioxide MT 500 B or Microtitanium Dioxide MT 600 B, by the company Degussa under the name P 25, by the company Wackherr under the name Transparent titanium oxide PW, by the company Miyoshi Kasei under the name UFTR, by the company Tomen under the name ITS and by the company Tioxide under the name Tioveil AQ.

The uncoated zinc oxide pigments are for example:

those sold under the name Z-Cote by the company Sunsmart;

those sold under the name Nanox by the company Elementis;

those sold under the name Nanogard WCD 2025 by the company Nanophase Technologies.

The coated zinc oxide pigments are for example:

those sold under the name Zinc Oxide CS-5 by the company Toshibi (ZnO coated with polymethylhydrogenosiloxane);

those sold under the name Nanogard Zinc Oxide FN by the company Nanophase Technologies (as a 40% dispersion in Finsolv TN, $C_{12}$-$C_{15}$ alkyl benzoate);

those sold under the name Daitopersion ZN-30 and Daitopersion ZN-50 by the company Daito (dispersions in cyclopolymethylsiloxane/oxyethylenated polydimethylsiloxane, containing 30% or 50% of zinc oxides coated with silica and polymethylhydrogenosiloxane);

those sold under the name NFD Ultrafine ZnO by the company Daikin (ZnO coated with perfluoroalkyl phosphate and copolymer based on perfluoroalkylethyl as a dispersion in cyclopentasiloxane);

those sold under the name SPD-Z1 by the company Shin-Etsu (ZnO coated with silicone-grafted acrylic polymer, dispersed in cyclodimethylsiloxane);

those sold under the name Escalol Z100 by the company ISP (alumina-treated ZnO dispersed in an ethylhexyl methoxycinnamate/PVP-hexadecene copolymer/methicone mixture);

those sold under the name Fuji ZnO-SMS-10 by the company Fuji Pigment (ZnO coated with silica and polymethylsilsesquioxane);

those sold under the name Nanox Gel TN by the company Elementis (ZnO dispersed at a concentration of 55% in C12-C15 alkyl benzoate with hydroxystearic acid polycondensate).

The uncoated cerium oxide pigments may be, for example, those sold under the name Colloidal Cerium Oxide by the company Rhône-Poulenc.

The uncoated iron oxide pigments are, for example, sold by the company Arnaud under the names Nanogard WCD 2002 (FE 45B), Nanogard Iron FE 45 BL AQ, Nanogard FE 45R AQ and Nanogard WCD 2006 (FE 45R) or by the company Mitsubishi under the name TY-220.

The coated iron oxide pigments are sold, for example, by the company Arnaud under the names Nanogard WCD 2008 (FE 45B FN), Nanogard WCD 2009 (FE 45B 556), Nanogard FE 45 BL 345 and Nanogard FE 45 BL or by the company BASF under the name Transparent Iron Oxide.

Mention may also be made of mixtures of metal oxides, in particular of titanium dioxide and of cerium dioxide, including the equal-weight mixture of titanium dioxide and cerium dioxide coated with silica, sold by the company Ikeda under the name Sunveil A, and also the mixture of titanium dioxide and zinc dioxide coated with alumina, silica and silicone, such as the product M 261 sold by the company Kemira, or coated with alumina, silica and glycerol, such as the product M 211 sold by the company Kemira.

According to the invention, coated or uncoated titanium oxide pigments are particularly preferred.

The titanium oxide may be in rutile and/or anatase form and/or in an amorphous or substantially amorphous form.

According to a preferred embodiment, the composite particles in spherical form contain a core comprising at least one organic material and/or at least one inorganic material, in which are included particles of inorganic UV-screening agent.

According to this embodiment, the particles of inorganic UV-screening agent are characterized by a mean elementary size generally of less than 200 nm. Advantageously, the metal oxide particles used have a mean elementary size of less than or equal to 0.15 µm.

As composite particles in spherical form corresponding to this variant, mention may be made of the products Sunsil TIN 50 and Sunsil TIN 40 sold by the company Sunjin Chemical. These spherical composite particles having a mean size between 2 and 7 µm are formed of $TiO_2$ encapsulated in a silica core.

Mention may also be made of the following particles:
spherical composite particles having a mean size of between 4 and 8 µm, containing $TiO_2$ and $SiO_2$ and having the trade name Eospoly TR, sold by the company Creations Couleurs,
composite particles containing $TiO_2$ and a styrene/alkyl acrylate copolymer matrix, sold under the name Eospoly UV TR22 HB 50 by the company Creations Couleurs,
composite particles containing $TiO_2$ and ZnO and a PMMA matrix and having the trade name Sun PMMA-T50, sold by the company Sunjin Chemical.

Among the composite particles in spherical form that may be used according to the invention, mention may also be made of the spherical composite particles containing $TiO_2$ and $SiO_2$, having the trade name STM ACS-0050510, supplied by the company JGC Catalysts and Chemical.

According to a preferred embodiment, the composite particles in spherical form contain an inorganic UV-screening agent covered with at least one layer of an organic and/or inorganic material. According to this embodiment, the particles of inorganic UV-screening agent are characterized by a mean elementary size generally of between 0.001 and 0.2 µm. Advantageously, the metal oxide particles used have a mean elementary size of between 0.01 and 0.15 µm.

According to a preferred embodiment, the composite particles in spherical form contain a core made of an organic and/or inorganic material, covered with at least one layer of inorganic UV-screening agent connected to the matrix by means of a binder.

According to this embodiment, the mean thickness of the layer of inorganic UV-screening agent is generally between 0.001 and 0.2 µm and preferably between 0.01 and 0.1 µm.

According to one particular form of this embodiment, the composite particles in spherical form can be constituted of:
i) spherical particles $A_1$ having a mean size of greater than 0.1 µm and less than 1 µm, more preferentially less than 0.6 µm and even more preferentially less than 0.4 µm, the surface of said particles $A_1$ being at least partially covered with at least one particulate solid UV-screening agent as defined previously;
ii) and optionally spherical particles $A_2$ having a mean size of greater than or equal to 2 µm, preferably greater than or equal to 3 µm, more preferentially greater than 4 µm and even better still greater than or equal to 5 µm, the surface of said particles $A_2$ being at least partially covered with at least one particulate solid UV-screening agent as defined previously.

The surface of said particles $A_1$ or $A_2$ can also be at least partially covered with at least one pulverulent colorant.

In particular, the pulverulent colorants are chosen from pigments and nacres, and mixtures thereof.

Preferably, the pulverulent colorants of the present invention are chosen from pigments. The pigments may be white or coloured, and mineral and/or organic.

According to a preferred embodiment, the pulverulent colorants of the present invention are chosen from mineral pigments.

The pulverulent colorant(s) can be used in the composite particles of the invention in proportions such that the ratio by weight of the particles $A_1$ or $A_2$/colorant(s) is from 50:50 to 90:10, preferably from 50:50 to 80:20 and more preferentially from 50:50 to 70:30.

Such mineral pigments will be disclosed further in the description.

Pigments

The term "pigments" should be understood as meaning white or coloured, mineral or organic particles of any shape, which are insoluble in the physiological medium, and which are intended to colour the composition.

The pigments may be white or coloured, and mineral and/or organic.

Among the mineral pigments that may be mentioned are titanium dioxide, optionally surface-treated, zirconium oxide or cerium oxide, and also zinc oxide, iron (black, yellow or red) oxide or chromium oxide, manganese violet, ultramarine blue, chromium hydrate and ferric blue, and metal powders, for instance aluminium powder and copper powder.

The core of the particles $A_1$ and the core of the particles $A_2$ are constituted of an inorganic material and/or of an organic material.

The inorganic material or the organic material may be hollow or porous. The porosity of the material may be characterized by a specific surface area of from 0.05 $m^2/g$ to 1500 $m^2/g$, more preferentially from 0.1 $m^2/g$ to 1000 $m^2/g$ and more preferentially from 0.2 $m^2/g$ to 500 $m^2/g$ according to the BET method.

The inorganic materials that may be used in the core of the spherical particles $A_1$ or $A_2$ according to the present invention may be chosen from the group formed by glass, silica and aluminium oxide, and mixtures thereof.

The organic materials that may be used to form the core of the particles $A_1$ or $A_2$ are chosen from the group formed by poly(meth)acrylates, polyamides, silicones, polyurethanes, polyethylenes, polypropylenes, polystyrenes, polycaprolactams, polysaccharides, polypeptides, polyvinyl derivatives, waxes, polyesters and polyethers, and mixtures thereof.

The particles $A_1$ are partially covered with at least one layer comprising at least one particulate UV-screening agent. Preferably, at least 10% of the surface of the particle is covered, preferably at least 50% and more preferentially at least 80%, and even better still 100% of the surface of the particle is covered with solid screening agent.

The thickness of the coating of the particle $A_1$ can depend on several factors, in particular on the size of the particle. Typically, the thickness can range from 0.001 to 0.2 µm, preferably from 0.005 to 0.18 µm and more preferentially from 0.01 to 0.150 µm.

If at least two layers of coating are present on the particle $A_1$, the thickness and the composition of the layers may be identical or different.

The layer(s) of coating may comprise other materials, such as colouring pigments. These materials may be present in an amount ranging from 1% to 50% of the total weight of the materials coating the particle $A_1$.

The spherical particles $A_2$ have a mean size of greater than or equal to 2 µm, preferably greater than or equal to 3 µm and more preferentially greater than 4 µm. The mean size can be limited to at most 50 µm, preferably at most 30 µm, more preferentially at most 20 µm and even more particularly at most 10 µm.

The mean particle size or the mean diameter is an arithmetic mean diameter and can be determined, for example, by calculating the mean of the dimensions of about 100 particles chosen on an image obtained by scanning electron microscopy.

The spherical particles $A_2$ may be hollow or solid and preferably solid.

According to one particularly preferred form, the core of the particles $A_1$ will be constituted of styrene copolymer and more preferentially of styrene/acrylate copolymer and more particularly of styrene/methylacrylate copolymer, for instance the product sold under the trade name Sunspheres by the company Rohm & Haas and also the product sold under the trade names SX859(A) and SX866(B) by the company JSR Corp in Japan.

According to one particularly preferred form, the core of the particles $A_2$ will be constituted of
- polymethacrylate and more particularly of poly(methyl methacrylate), for instance the product sold under the trade name MR-7GC by Soken in Japan,
- polyamide, for instance the product sold under the trade name SP-500 by Toray or Orgasol by Arkema,
- polytetrafluoroethylene, such as the commercial product sold under the name Ceridust 9205F by Clariant.

More preferably the core of the particles $A_2$ is constituted of poly(methyl methacrylate).

The weight ratio of the particles $A_1$/particles $A_2$ can be from 10:90 to 90:10, preferably from 20:80 to 80:20 and more preferentially from 30:70 to 70:30.

The weight ratio of the particles $A_1$ to the particulate UV-screening agent can be from 10:90 to 90:10, preferably from 20:80 to 80:20 and more preferentially from 30:70 to 70:30.

The weight ratio of the particles $A_1$/particles $A_2$/particulate UV-screening agent can be from 20:50:30 to 50:20:30, preferably from 35:15:50 to 15:35:50, more preferentially from 10:20:70 to 20:10:70 and more particularly 50:20:30 or 35:15:50.

According to one particularly preferred form, the composite particle in spherical form comprise:
i) spherical particles $A_1$ having a mean size of greater than 0.1 µm and less than 1 µm, more preferentially less than 0.6 µm and even more preferentially less than 0.4 µm, the surface of said particles $A_1$ being at least partially covered with titanium dioxide particles and the core of the particles being constituted of styrene/methyl methacrylate copolymer;
ii) spherical particles $A_2$ having a mean size of greater than or equal to 2 µm, preferably greater than or equal to 3 µm, more preferentially greater than 4 µm and even better still greater than or equal to 5 µm, the surface of said particles $A_2$ being covered with at least titanium dioxide particles and the core of the particles being constituted of poly(methyl methacrylate).

Mechanofusion Process

The composite particle in spherical form according to the invention can be prepared by subjecting the following to a mechanofusion process:
- the spherical particles $A_1$ having a mean size of greater than 0.1 µm and less than 1 µm, more preferentially less than 0.6 µm and even more preferentially less than 0.4 µm,
- and optionally the spherical particles $A_2$ having a mean size of greater than or equal to 2 µm, preferably greater than or equal to 3 µm, more preferentially greater than 4 µm and even better still greater than or equal to 5 µm, and
- at least one solid UV-screening agent as previously defined,
- and optionally the additional UV-screening agent(s) and/or the pulverulent colorant(s) as previously defined.

A mechanofusion process consists of a process in which a mechanical power, such as a compressive force, a frictional force or a shear force, is exerted on a plurality of elements, causing the fusion of said elements.

The mechanofusion process can be performed with a device comprising a rotary chamber and an internal part attached to a scraper, such as the device sold under the trade name Hosokawa Micron Corporation in Japan.

A process of hybridization by mechanofusion will preferably be used.

The hybridization process was developed in the 1980s. It is a type of mechanofusion process in which a strong mechanical power is applied to a plurality of particles in order to cause a mechanochemical reaction so as to form composite particles.

According to the hybridization process, the mechanical power is produced by a high-speed rotor which can have a diameter ranging from 10 cm to 1 m and which can rotate at a speed ranging from 1000 to 10 000 revolutions/minute. The hybridization process can be carried out in air or under a dry atmosphere. Indeed, the high-speed rotation of the rotor can generate a high-speed air flow in proximity to the rotor. Liquid materials can be subjected to the hybridization process in the presence of solid materials.

The hybridization process can be carried out using a hybridization system sold under the trade name Nara Machinery, in which at least two types of particles, generally particles comprising a core and fine particles, are introduced into a hybridizer equipped with a high-speed rotor having a plurality of blades in a dry chamber, and the particles are dispersed in the chamber and mechanical and thermal energy is produced on the particles (compression, friction and shear) for a short period such as from 1 to 10 minutes and preferably from 1 to 5 minutes. This results in particles of one type (fine particles) integrated on or attached to particles of another type (i.e. particles comprising a core) so as to form composite particles. It is preferable for the particles to be subjected to an electrostatic treatment, for example by shaking them so as to form an "ordered mixture" in which particles of one type are spread out so as to cover the particles of the other type. The hybridization process can be carried out using a Theta composer sold by Tokuju Corporation.

The hybridization process can be carried out using a device of the Composi Hybrid or Mechano Hybrid type sold by Nippon Coke.

According to the invention, the hollow particles $A_1$, the particles $A_2$, the particulate screening agent(s), the optional colouring pigment(s) and the optional additional screening agent(s) are introduced into a hybridizer so as to form a composite pigment.

The hybridization process can be carried out using a rotor rotating at approximately 8000 rpm for approximately 3 minutes.

Preferably, the content of composite particles in spherical form in the composition according to the invention ranges from 1% to 70%, preferably from 1.5% to 50% and preferably from 2% to 40% by weight relative to the total weight of the cosmetic composition.

Anti-Oxidation Active Ingredient

The composition of the present invention comprises at least one anti-oxidation active ingredient. The ingredients are used for protecting the keratin materials, especially the skin, from pro-oxidation. A compound of formula (I) can be used in the composition according to the present invention as an anti-oxidation active ingredient.

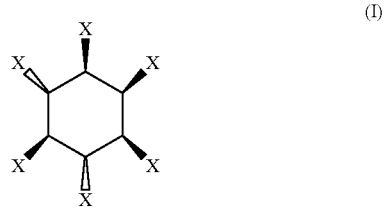

(I)

In formula (I), each X independently represents —OPO$_3$Y, wherein Y is selected from hydrogen, Li, Na and K.

In an embodiment of the present, a plant seed extraction containing the compound according to formula (I) is used as an anti-oxidation active ingredient. Such a plant seed extraction can be for example Phytovityl® sold by the company Solabia.

Phytovityl® is an active vegetal fraction obtained from controlled and specific extraction of corn seeds whose major ingredients are involved in the cellular metabolism. Phytovityl® is composed myo-inositol derivative in the phytate form. Phytovityl® has anti-free radical activity and anti-pollution effect.

A dimer peptide according to formula (II) can also be used in the composition according to the present invention as anti-oxidation active ingredient.

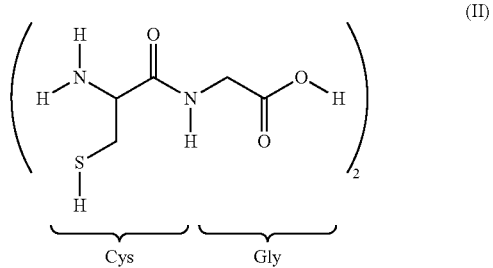

(II)

In an embodiment, a seed extract containing the above dimmer peptide is used. In an example, Phytoquintescine™ is used as an anti-oxidation active ingredient sold by the company ISP Vincience (Ashland).

Phytoquintescine™ (INCI: HYDROLYZED TRITICUM MONOCOCCUM SEED EXTRACT) is extracted by a specific extraction process, selective hydrolysis and purification. This process allows to select, isolate and concentrate a dimer peptide with antioxidant properties. Phytoquintescine is perfectly adapted to day care products, and specifically, to anti-pollution and anti-stress products.

Tocopherol and/or its derivatives can be used in the composition according to the present invention. Suitable tocopherol derivatives may include for example, sodium vitamin E phosphate (VEP), lauryl imino dipropionic acid tocopheryl phosphate, tocopheryl glucoside, tocopheryl succinate, tocophersolan (tocopheryl polyethylene glycol 1000 succinate), disodium lauriminodipropionate tocopheryl phosphates, tocophereth-5, 10, 12, 18 and 50 (polyethylene glycol tocopheryl ethers). Preferred tocopherol derivatives includes sodium vitamin E phosphate, lauryl imino dipropionic acid tocopheryl phosphate, and disodium lauriminodipropionate tocopheryl phosphates.

More preferably, tocopherol is used in the present invention. Examples of the tocopherol which is suitable to the present invention is, for example, DI Alpha Tocopherol sold by the company DSM Nutritional Products.

The amount of anti-oxidation active ingredient in the compositions of the invention preferably ranges from 0.001% to 10% by weight, more preferably from 0.001% to 5% by weight, even more preferably from 0.002% to 4%, in particular from 0.002% to 2% by weight, relative to the total weight of the composition.

Polysaccharide

Advantageously, a polysaccharide can be used in the composition according to the present invention is a polymer of natural origin.

Furthermore, a polysaccharide used according to the present invention may also, or alternatively, be in linear or branched form.

For the purposes of this invention, the term "branched" means a polymer including at least one saccharide unit and/or a polysaccharide sequence, is laterally attached to the main chain.

According to one advantageous embodiment of the present invention, a polysaccharide used according to the present invention contains at least 25% by weight of fucose and 25% by weight of glucuronic acid, based on the total weight of the polymer.

Specifically, a polysaccharide can be implemented according to the present invention contains from 25% to 80% by weight of fucose and 25% to 80% by weight of glucuronic acid, based on the total weight of the polymer.

According to another preferred embodiment, a polysaccharide contains from 1 to 50% by weight of glucose, based on the total weight of the polymer.

According to the invention, the term saccharide or polysaccharide polymer (or polysaccharide), a polymer comprising at least three saccharide units or derivatives thereof, at least one kind of fucose, glucose of a type and a glucuronic acid type, said units being linked together through O-glycosidic bonds.

More particularly, fucose and glucose are present in the L form and D, respectively.

In the context of the present invention, be used indifferently "radical" or terms "unit" for a monosaccharide derivative or pattern, forming an polysaccharide according to the invention.

Under saccharide units or groups, can be made, for example addition fucose, glucose and glucuronic acid, such as trioses cetotrioses (dihydroxyacetone), the aldotrioses (glyceraldehyde); tetroses such as cetotetroses (Erythrulose), the aldotetrose (erythrose, threose); pentoses such as ketopentoses (ribulose, xylulose), the aldopentose (arabinose, lyxose, ribose, xylose), the desoxyose(deoxyribose); hexoses such as ketohexoses (fructose, psicose, sorbose, tagatose) aldohexoses(allose, altrose, galactose, gulose, idose, mannose, talose) deoxyoses(fuculose, pneumose, quinovose, rhamnose); the heptoses (glucoheptose, idoheptulose, mannoheptulose, sedoheptulose, taloheptulose) or the derivatives thereof or octoses.

Derivatives by means of a saccharide unit, a unit as defined above, further having undergone a chemical modification resulting in the presence of ancillary chemical groups and/or absence of initially present in the considered chemical groups monosaccharide. In this respect, one can for example include glucuronic acid from glucose, oxidized on its carbon number 6.

A particularly suitable polysaccharide of the present invention, is formed solely of units fucose, glucose and glucuronic acid.

Advantageously, the saccharide units implemented within a polysaccharide according to the invention can form a saccharide sequence that is repeated in said polymer.

Thus, a polymer used in the present invention preferably comprises at least one fucose unit, a glucuronic acid unit and two glucose units, present in the form of a tetrasaccharide repeating sequence.

Advantageously, such a sequence is repeated at least 100 times.

In a preferred variant, the polymer according to the invention is considered a compound comprising at least one tetrasaccharide sequence following formula:

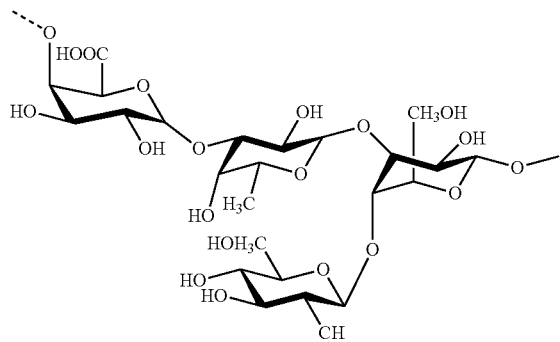

In a preferred embodiment, the saccharide polymer has a molecular weight ranging from 104 to 108 Dalton and in particular of 5104-5107 Dalton.

Such a polymer is particularly marketed under the name Glycofilm 1.5 P® (INCI name: Biosaccharide Gum-4), marketed by SOLABIA.

Glycofilm 1.5 P® is an anionic polysaccharide (mean molecular weight $2\times10^6$), prepared through biotechnology from plant material. It is a branched desacetylated structure with saccharide sequence comprises glucuronic acid (I), L-fucose (II) and D-glucose (III, IV) as follows:

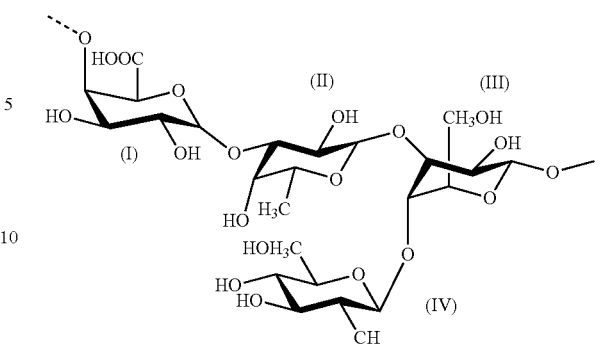

Glycofilm 1.5 P® is a film-protective active ingredient which, just like a coat of mail or a second skin, allows limiting the skin external aggressions, notably the ones induced by U.V. rays, pollution, heavy metals and the intensive use of surfactants.

Apart from its ability to form a three-dimensional biomatrix at the skin surface, Glycofilm 1.5 P® also provides textural properties which optimize the smoothness of cosmetic formula and emphasize the resulting well-being feeling.

This polymer is already proposed for its anti-UV and anti-pollution properties. However, it has, to the knowledge of the inventors, never been described for its firming properties.

In general, the polysaccharides of the invention may be commercially available or may be obtained, for example, by culturing yeast in standard operating conditions, clearly within the general knowledge of those skilled in the art.

For example, the Biosaccharide Gum-4 can be obtained by bacterial fermentation, sorbitol from vegetable and autolytic yeast extract.

The amount of the at least one polysaccharide in the compositions of the invention is up to 6% by weight, preferably ranges from 0.0001% to 5% by weight, more preferably from 0.001% to 4.5% by weight, even more preferably from 0.005% to 2% by weight, relative to the total weight of the composition.

Pigments

"Pigments" are white or coloured, organic or inorganic, non-interference particles which are insoluble in aqueous and non-aqueous media and are intended for colouring the composition.

Not included, therefore, in this regard are nacres (natural or otherwise), metallic pigments, interference pigments, etc.

Inorganic pigments which can be used in the invention include oxides or dioxides of titanium, zirconium or cerium, and also oxides of zinc, iron or chromium, Prussian blue, manganese violet, ultramarine blue and chromium hydrate, and mixtures thereof.

The organic pigments which can be used in the invention include D & C pigments, lakes based on cochineal carmine, and on barium, strontium, calcium and aluminium, or else the diketopyrrolopyrroles (DPP) which are described in documents EP-A-542 669, EP-A-787 730, EP-A-787 731 and WO-A-96/08537.

According to one preferred embodiment, use will be made of inorganic pigments, selected more particularly from titanium oxides and iron oxides (especially yellow, black and red), advantageously coated with at least one hydrophobic agent.

The pigments of the invention are preferably wholly or partly surface-treated with a hydrophobic agent, more particularly with a fluoro, fatty acid or amino acid, or silicone compound, or a mixture thereof.

Their initial particle size D [0.5] is especially less than 20 µm, preferably between 0.4 and 10 µm, end points included.

By way of example, the hydrophobic treatment agent may be selected from fatty acids such as stearic acid; metal soaps such as aluminium dimyristate and the aluminium salt of hydrogenated tallow glutamate; perfluoroalkyl phosphates and polyhexafluoropropylene oxides; perfluoropolyethers; amino acids; N-acylamino acids or salts thereof; lecithin, isopropyl trisostearyl titanate, isostearyl sebacate, and silicone compounds such as dimethicones or polydimethylsiloxanes, and mixtures thereof.

The hydrophobic treatment agent is preferably selected from perfluoroalkyl phosphates, polyhexafluoropropylene oxides, perfluoropolyethers, amino acids, N-acylamino acids or salts thereof, isopropyl trisostearyl titanate, and mixtures thereof.

More preferably, the hydrophobic agent is selected from perfluoroalkyl phosphates, N-acylamino acids or salts thereof, isopropyl trisostearyl titanate, and mixtures thereof.

The surface-treated pigments may be prepared according to chemical, electronic, chemomechanical or mechanical surface treatment techniques that are well known to the skilled person. It is also possible to use commercial products.

The surface agent may be absorbed or adsorbed on the pigments by solvent evaporation, chemical reaction and creation of a covalent bond.

According to one version, the surface treatment comprises a coating of the pigments.

The coating may represent from 0.1 to 10% by weight and more particularly from 1% to 5% by weight, of the total weight of the coated pigments.

Coating may be carried out, for example, by adsorption of a liquid surface agent on the surface of the pigments, by simple mixing with stirring of the pigments and of said surface agent, optionally under hot conditions, prior to the incorporation of the pigments into the other ingredients of the care or makeup composition.

Coating may be carried out, for example, by chemical reaction of a surface agent with the surface of the pigments and creation of a covalent bond between the surface agent and the pigments. This method is described especially in U.S. Pat. No. 4,578,266.

Amino Acid or Fatty Acid Treatment Agent

The hydrophobic treatment agent may be selected from fatty acids, such as stearic acid; metal soaps, such as aluminium dimyristate and the aluminium salt of hydrogenated tallow glutamate; amino acids; N-acylamino acids or salts thereof; lecithin, isopropyl trisostearyltitanate (or alternatively called ITT), and mixtures thereof.

The N-acylamino acids may comprise an acyl group having from 8 to 22 carbon atoms, such as, for example, a 2-ethylhexanoyl, caproyl, lauroyl, myristoyl, palmitoyl, stearoyl or cocoyl group. The salts of these compounds may be the aluminium, magnesium, calcium, zirconium, zinc, sodium or potassium salts. The amino acid may be, for example, lysine, glutamic acid or alanine.

The fatty acids in the present invention are more particularly acids with hydrocarbon chains having from 1 to 30 carbon atoms, preferably having from 5 to 18 carbon atoms. The hydrocarbon chain may be saturated, monounsaturated or polyunsaturated.

Examples of pigments coated with fatty acids include those containing the disodium stearoylglutamate/aluminium hydroxide pairing, these being sold in particular under the trade name NAI-TAO-77891, NAI-C33-8073-10, NAI-C33-8075, NAI-C47-051-10, NAI-C33-115, NAI-C33-134, NAI-C33-8001-10, NAI-C33-7001-10, NAI-C33-9001-10 from the company Miyoshi Kasei.

Examples of pigments treated with isopropyltitanium triisostearate (ITT) include those sold under the trade name BWBO-12 (Iron oxide C177499 and isopropyl titanium triisostearate), BWYO-12 (Iron oxide C177492 and isopropyl titanium triisostearate) and BWRO-12 (Iron oxide C177491 and isopropyl titanium triisostearate) by the company Kobo.

Preferably, pigments coated with disodium stearoylglutamate/aluminium hydroxide are used in the present invention.

Preferably, the pigment is present in the composition of the invention in an amount of generally from 1% to 30% by weight, preferably from 2% to 25% by weight, and more preferably from 5% to 20% by weight, relative to the total weight of the composition.

Adjuvants

The composition according to the invention may further comprise additional adjuvants commonly used in the envisaged application field.

Mention may be made especially of organic solvents, especially $C_1$-$C_6$ alcohols and $C_2$-$C_{10}$ carboxylic acid esters; carbon-based and/or silicone oils, of mineral, animal and/or plant origin; waxes, additional pigments, fillers, colorants, surfactants, emulsifiers, co-emulsifiers; cosmetic or dermatological active agents, additional UV filters, polymers, hydrophilic or lipophilic gelling agents, thickeners, preserving agents, fragrances, bactericides, ceramides, odor absorbers, antioxidants.

Fillers

A composition in accordance with the invention may comprise at least one filler of organic or mineral nature.

The term "filler" should be understood to mean colourless or white solid particles of any shape which are in a form that is insoluble and dispersed in the medium of the composition. They are mineral or organic in nature and make it possible to confer softness and mattness on the composition and a uniform makeup result.

The fillers used in the compositions according to the present invention may be in lamellar, globular or spherical form, in the form of fibers or in any other intermediate form between these defined forms.

The fillers according to the invention may or may not be surface-coated, and in particular they may be surface-treated with silicones, amino acids, fluoro derivatives or any other substance that promotes the dispersion and compatibility of the filler in the composition.

Among the mineral fillers that can be used in the compositions according to the invention, mention may be made of talc, mica, trimethyl siloxysilicate, kaolin, bentone, calcium carbonate, magnesium hydrogen carbonate, hydroxyapatite, boron nitride, perlite, glass or ceramic microcapsules, and mixtures thereof.

Among the organic fillers that can be used in the compositions according to the invention, mention may be made of polyamide powders (Nylon® Orgasol from Atochem), poly-β-alanine and polyethylene powders, polytetrafluoroethylene (Teflon® from DuPont) powders, lauroyllysine, starch, modified or unmodified, specially oxidized ester modified starch, such as acetylated oxidized starch sold under the tradename GF-A390 by the company Suzhou Gaofeng, tetrafluoroethylene polymer powders, hollow polymer microspheres, such as Expancel (Nobel Industrie), metal soaps derived from organic carboxylic acids containing from 8 to 22 carbon atoms, preferably from 12 to 18 carbon atoms, for example zinc stearate, magnesium stearate or lithium stearate, zinc laurate, magnesium myristate, Polypore® L 200 (Chemdal Corporation), silicone resin microbeads (Tospearl® from Toshiba, for example), polyurethane powders, in particular powders of crosslinked polyurethane comprising a copolymer, said copolymer comprising trimethylol hexyllactone, for instance the hexamethylene diisocyanate/trimethylol hexyllactone polymer sold under the name Plastic Powder D-400® or Plastic Powder D-800® by the company Toshiki, carnauba microwaxes, such as the product sold under the name MicroCare 350® by the company Micro Powders, microwaxes of synthetic wax, such as the product sold under the name MicroEase 114S® by the company Micro Powders, microwaxes constituted of a mixture of carnauba wax and of polyethylene wax, such as those sold under the names MicroCare 300® and 310® by the company Micro Powders, microwaxes constituted of a mixture of carnauba wax and of synthetic wax, such as the product sold under the name MicroCare 325® by the company Micro Powders, polyethylene microwaxes, such as those sold under the names Micropoly 200®, 220®, 220L® and 250S® by the company Micro Powders; and mixtures thereof.

Advantageously, the filler suitable for the composition of the present invention is perlite. The perlite is an off-white solid powder composed of inert amorphous vitreum particles, whose main components are potassium, sodium, and aluminosilicate without peculiar smell. The perlite has anti-sweet and oil control ability, thus the introduction of perlite in the formula can ensure the long wear of makeup result and also longer protection delivered by this composition.

Preferably, the at least one filler is present in the composition of the present invention from 0 to 20% by weight, preferably from 0.01% to 10%, more preferably from 0.1% to 5% by weight, relative to the total weight of the composition.

These additional adjuvants may be present in the composition in a proportion of from 1% to 50% by weight and especially from 2% to 30% by weight relative to the total weight of the composition. Depending on their nature, these adjuvants may be introduced into the fatty phase or into the aqueous phase of the composition, or into lipid vesicles. In any case, these adjuvants, and the proportions thereof, will be chosen by a person skilled in the art such that the advantageous properties of the compounds according to the invention are not, or are not substantially, adversely affected by the envisaged addition.

The cosmetic composition according to the present application can protect the skin against UV radiation and pro-oxidation.

The composition is stable under various temperature, such as 4° C., room temperature(25° C., 2 months), 45° C., and 45° C. (2 months).

According to another aspect of the present invention, there is provided a process for preparing a composition according to the present invention comprising mixing at least one UV filter, at least one SPF booster and/or at least one composite particle in spherical form, and at least one anti-oxidation active ingredient.

According to one aspect of the present invention, there is provided use of a combination of at least one UV filter, at least one SPF booster and/or at least one composite particle in spherical form, and at least one anti-oxidation active ingredient in producing a composition for protecting the skin from UV radiation and pro-oxidation.

Galenical Form

The compositions according to the invention as defined above may be in any of the galenical forms conventionally used for topical application, and in particular in the form of aqueous or aqueous-alcoholic solutions, of oil-in-water (O/W) or water-in-oil (W/O) or multiple (triple: W/O/W or O/W/O) emulsions, of aqueous gels, or of dispersions of a fatty phase in an aqueous phase by means of polymeric microparticles such as microspheres and microcapsules, or of lipid vesicles of ionic and/or nonionic type (liposomes, niosomes, oleosomes), of microemulsions or of thin films.

In addition, the compositions used according to the invention may be more or less fluid and may have the appearance of a white or coloured cream, an ointment, a milk, a lotion, a serum, a paste or a foam. They may be optionally applied to the skin in the form of an aerosol.

In a preferred embodiment, the composition is a make-up product, such as a BB cream, a foundation, a face powder, a lip gloss, a lipstick, an eyeshadow.

In another embodiment, the composition is a skin-care product, such as lotions, milks, creams of thicker or thinner consistency, gels and cream-gels. They may optionally be packaged as an aerosol and take the form of a foam or spray. Unless otherwise indicated, all numbers expressing quantities of ingredients, reaction conditions, and so forth used in the specification and claims are to be understood as being modified in all instances by the term "about."

Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible.

Any numerical value, however, inherently contain certain errors necessarily resulting from the standard deviation found in their respective measurements. The following examples are intended to illustrate the invention without limiting the scope as a result.

The percentages are given on a weight basis.

The invention will now be illustrated by means of the following non-limiting examples. The amounts of the ingredients in the following formulation examples are expressed as % by weight related back to the entire formulation.

EXAMPLES

Example 1-6: Preparation Examples

The following formulations were prepared following the steps of:

Mixing components for phase A listed in the following table while heating the mixture to 70° C. for 5 minutes, and cooling down to 25° C., until the mixture is homogeneous;

Mixing components for phase B at 25° C. until homogeneity;

Adding phase B to phase A listed in the following table while homogenizing for 15 minutes under 25° C., with the speed of 2500 rpm, using homogenizer Turbolab 2500 sold by the company Piere Guerin Technologie under the tradename Moritz.

| | | | | concentration | | | | | |
|---|---|---|---|---|---|---|---|---|---|
| Phase | Comercial name | supplier | INCI NAME | Ex. 1 (inventive) | Ex. 2 (inventive) | Ex. 3 (inventive) | Ex. 4 (inventive) | Ex. 5 (inventive) | Ex. 6 (comparative) |
| A | ABIL EM 90 | EVONIK GOLDSCHMIDT | CETYL PEG/PPG-10/1 DIMETHICONE | 3 | 3 | 3 | 3 | 3 | 3 |
| B | BALANCE LIPIDS, TYPE 13B | NESTLE WORLD TRADE CORPORATION | XANTHAN GUM | 0.15 | 0.15 | 0.15 | 0.15 | 0.15 | 0.15 |
| A | ISOLAN GI 34 | EVONIK GOLDSCHMIDT | POLYGLYCERYL-4 ISOSTEARATE | 1 | 1 | 1 | 1 | 1 | 1 |
| A | NAI-C33-9001-10 | MIYOSHI KASEI | IRON OXIDES (and) DISODIUM STEAROYL GLUTAMATE (and) ALUMINUM HYDROXIDE | 0.95 | 0.95 | 0.95 | 0.95 | 0.95 | 0.95 |
| A | NAI-C33-8001-10 | MIYOSHI KASEI | IRON OXIDES (and) DISODIUM STEAROYL GLUTAMATE (and) ALUMINUM HYDROXIDE | 0.33 | 0.33 | 0.33 | 0.33 | 0.33 | 0.33 |
| A | KSG 16 | SHIN ETSU | DIMETHICONE (and) DIMETHICONE/VINYL DIMETHICONE CROSSPOLYMER | 3.1 | 3.1 | 3.1 | 3.1 | 3.1 | 3.1 |
| B | SEL GRAIN | BIOTECHMARINE | SODIUM CHLORIDE | 0.7 | 0.7 | 0.7 | 0.7 | 0.7 | 0.7 |
| B | | | WATER | QS 100 | QS 100 | QS 100 | QS 100 | QS 100 | QS 100 |
| A | | | METAPIGMENT* | 2 | 2 | 2 | 2 | 2 | 2 |
| A | DM-FLUID-2CS | SHIN ETSU | DIMETHICONE | 21.2 | 21.2 | 21.2 | 20.7 | 21.2 | 21.2 |
| A | Parsol MCX | DSM Nutritional Products | ETHYLHEXYL METHOXYCINNAMATE | 6 | 6 | 6 | 6 | 6 | 6 |
| A | BWBO-12 | Kobo | IRON OXIDES (and) DISODIUM STEAROYL GLUTAMATE (and) ALUMINUM HYDROXIDE | 0.22 | 0.22 | 0.22 | 0.22 | 0.22 | 0.22 |
| A | NAI-TAO-77891 | Miyoshi Kasei | TITANIUM DIOXIDE (and) DISODIUM STEAROYL GLUTAMATE (and) ALUMINUM HYDROXIDE | 12.5 | 12.5 | 12.5 | 12.5 | 12.5 | 12.5 |
| B | PHYTO-QUINTESCINE G | ISP VINCIENCE (ASHLAND) | HYDROLYZED TRITICUM MONOCOCCUM SEED EXTRACT | 0.003 | — | — | 0.003 | — | — |
| B | PHYTOVITYL C | SOLABIA | ZEA MAYS (CORN) KERNEL EXTRACT | — | 0.005 | — | 0.005 | — | — |
| A | DL ALPHA TOCOPHEROL (0410276) | DSM NUTRITIONAL PRODUCTS | TOCOPHEROL | — | — | 0.5 | 0.5 | — | — |
| A | | | ELLAGIC ACID | — | — | — | — | — | 0.5 |
| B | GLYCOFILM 1.5P | SOLABIA | BIOSACCHARIDE GUM-4 | — | — | — | — | 0.01 | — |

*composite particle in spherical form, composed of 35 wt % of particles $A_1$ (styrene/acrylate copolymer) of 350 nm, 15 wt % of particles $A_2$ (PMMA) of 6 μm and 50 wt % of particulate UV-screening agent (TiO2) of 15 nm.

Example 7: Evaluation Example

Evaluations of the anti UV radiation, anti-oxidation effects, as well as the stabilities, including in vivo SPF tests and in vivo PPD tests, in-vitro anti-oxidation tests, and stability tests of the examples 1 to 6 were performed.

The in vivo SPF tests, the Sun Protection Factor (SPF) of the examples 1 to 6 were evaluated on human skin as defined by the FDA Sunscreen Final Rule; 21 CFR Parts 201 and 310, RIN 0910-AF43, Labeling and Effectiveness Testing; Sunscreen Drug Products For Over-the Counter Human Use [FR Doc. 2011-14766 Filed Jun. 16, 2011; Publication Date: Jun. 17, 2011] using a Xenon arc solar simulator as the UV source.

The in vivo PPD tests of the examples 1 to 6 were conducted according to the Japan Cosmetic Industry Association-J.C.I.A-Measurement Standards for UVA Protection Efficacy issued Nov. 21, 1995 and effective as of Jan. 1, 1996. The UVAPPD sun protection factor (UVAPPD SPF) is expressed mathematically by the ratio of the UV-A radiation dose necessary to reach the pigmentation threshold with the UV-screening agent (MPPDp) to the UV-A radiation dose necessary to reach the pigmentation threshold without UV-screening agent (MPPDnp).

The principle of the in-vitro anti-oxidation test used was determined via the determination of squalene and its product of photo-oxidation efficiency of an asset against this form of photo-peroxidation.

The test made use of squalene in the presence of a photosensitizer, hematoporphyrin. Under the action of UVA, haematoporphyrin passes an excited state. By successive reaction of singlet oxygen ($^1O_2$) was generated. This highly reactive form of oxygen degraded squalene oxidation of double bonds and breaking of these bonds and the formation of degradation products, peroxides squalene.

Under the test, exposure squalene associated with hematoporphyrin was performed in the presence of compositions obtained according to Examples 1-6.

Squalene is one of lipids representative of sebaceous activity and the formation of squalene peroxide reflects the degree of sebum superficial damage. Expose the lipids with UVA, a part of squalene transform into peroxide squalene. Using LC/DAD&MS/MS to quantify the ratio of peroxide squalene to squalene for both the sebum treated with placebo and treated with the examples, calculate the change of ratio and express as inhibition. The higher inhibition represents the better anti-oxidation effect of the example.

The reaction medium is ethanol.

The (hematoporphyrin squalene/(80/20 v:v)+each composition) mixture is exposed for 45 min to UVA (UVA 5 joules/cm²).

The dosage of squalene and squalene peroxides is done by HPLC/UV.

Product Reference:
Squalene [Sigma S-3626].
Haematoporphyrin Free Base (approx. 70%) [Sigma-ref H-7253]

The stability tests were conducted by leaving the examples 1-6 under 4° C., 25° C., 37° C., and 45° C. for 2 months, and investigating the appearance of the examples.

The results were as follows:

|  | Example | | | | | |
| --- | --- | --- | --- | --- | --- | --- |
| Test | Ex. 1 (inventive) | Ex. 2 (inventive) | Ex. 3 (inventive) | Ex. 4 (inventive) | Ex. 5 (inventive) | Ex. 6 (Comparative) |
| SPF | 60.7 | 60.4 | 61.2 | 63.6 | 65.3 | 58.8 |
| PPD | 20.1 | 20.9 | 21.6 | 22.9 | 24.1 | 18.7 |
| Anti-oxidation (% inhibition) | 87% | 88% | 87% | 93% | 86% | 84% |
| Stability | stable | stable | stable | stable | stable | Unstable under 45° C., emulsion broken |

Comments:

The results shows that as compared with the comparative example 6, the examples 1-5 according to the present invention have improved performance on sun protection, anti-oxidation effect and are stable over time.

While illustrative examples of the invention have been described above, it is, of course, understood that many and various modifications will be apparent to those of ordinary skill in the relevant art, or may become apparent as the art develops, in the light of the foregoing description. Such modifications are contemplated as being within the spirit and scope of the invention or inventions disclosed in this specification.

We claim:

1. A composition, comprising:
   a) at least one UV filter;
   b) spherical composite particles comprising:
      i) spherical particles $A_1$ having a mean size of greater than 0.1 microns and less than 1 micron, the surface of said particles $A_1$ being at least partially covered with titanium dioxide particles and the core of the particles comprising styrene/methyl methacrylate copolymer; and
      ii) spherical particles $A_2$ having a mean size of greater than or equal to 2 microns, the surface of said particles $A_2$ being covered with at least titanium dioxide particles and the core of the particles comprising poly (methyl methacrylate); and
   c) at least one anti-oxidation active ingredient selected from the group consisting of I) a compound according to formula (I)

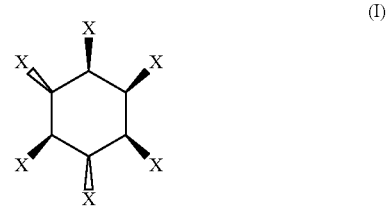

wherein
each X independently represents —$OPO_3Y$, wherein Y is hydrogen, Li, Na, or K;

II) a dimer peptide according to formula (II):

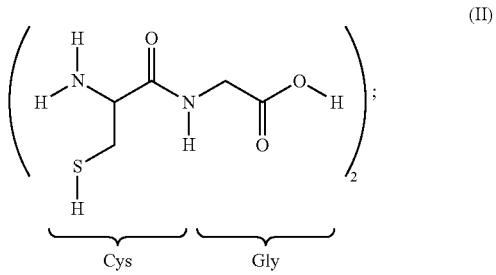

III) a tocopherol or a derivative thereof; and
IV) a mixture thereof.

2. The composition according to claim 1, wherein the at least one UV filter is selected from the group consisting of an organic UV filter, an inorganic UV filter, or a mixture thereof.

3. The composition according to claim 2, wherein the at least one UV filter comprises from 0.5% to 20% by weight of at least one organic UV filter, relative to a total weight of the composition.

4. The composition according to claim 2, wherein the at last one UV filter comprises from 0.01% to 10% by weight of at least one inorganic UV filter, relative to a total weight of the composition.

5. The composition according to claim 1, wherein the composition further comprises an SPF booster which is made from at least one material selected from the group consisting of a copolymer of (meth)acrylic acid, (meth)acrylates, and/or styrene; glass; silica; or a mixture thereof.

6. The composition according to claim 5, wherein the SPF booster is in a form of a particle with a particle size from 100 to 380 nm.

7. The composition according to claim 1, wherein the composite particle contains a core comprising at least one organic material, in which are included particles of particulate UV-screen agent.

8. The composition according to claim 1, wherein a material of the core of the spherical composite particles is selected from the group consisting of a poly(meth)acrylate, a polyamide, a silicone, a polyurethane, a polyethylene, a polypropylene, a polystyrene, a polycaprolactam, a polysaccharide, a polytetrafluoroethylene, a polypeptide, a polyvinyl derivative, a wax, a polyester, a polyether, and a mixture thereof.

9. The composition according to claim 1, wherein the particulate UV-screening agent is inorganic and is a metal oxide, in coated or uncoated form.

10. The composition according to claim 5, comprising from 0.1% to 10% by weight of the SPF booster and the composite particle in spherical form, relative to a total weight of the composition.

11. The composition according to claim 1, comprising from 0.001% to 10% by weight of the anti-oxidation active ingredient, relative to a total weight of the composition.

12. The composition according to claim 1, further comprising at least one polysaccharide.

13. The composition of claim 12, wherein the at least one polysaccharide is a gum.

14. The composition according to claim 1, further comprising at least one pigment.

15. The composition according to claim 1, further comprising at least one filler of mineral or organic nature.

16. The composition according to claim 1, which is in a form of an aqueous or aqueous-alcoholic solution, of an oil-in-water or a water-in-oil or a multiple emulsion, of an aqueous gel, of a dispersion of a fatty phase in an aqueous phase via polymeric microparticles, of a lipid vesicle of ionic and/or nonionic type, of a microemulsion, or of a thin film.

17. A method for preparing the composition according to claim 1, the method comprising mixing the at least one UV filter, the at least one composite particle in spherical form, and the at least one anti-oxidation active ingredient.

18. A method for producing a composition for protecting a keratin material from UV radiation and pro-oxidation, the method comprising:

mixing a) at least one UV filter;

b) spherical composite particles comprising:

i) spherical particles $A_1$ having a mean size of greater than 0.1 microns and less than 1 micron, the surface of said particles $A_1$ being at least partially covered with titanium dioxide particles and the core of the particles comprising styrene/methyl methacrylate copolymer; and ii) spherical particles $A_2$ having a mean size of greater than or equal to 2 microns, the surface of said particles $A_2$ being covered with at least titanium dioxide particles and the core of the particles comprising poly(methyl methacrylate)

c) at least one anti-oxidation active ingredient selected from the group consisting of I) a compound according to formula (I)

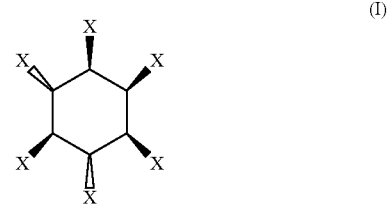

wherein each X independently represents —OPO$_3$Y, wherein Y is hydrogen, Li, Na, or K;

II) a dimer peptide according to formula (II):

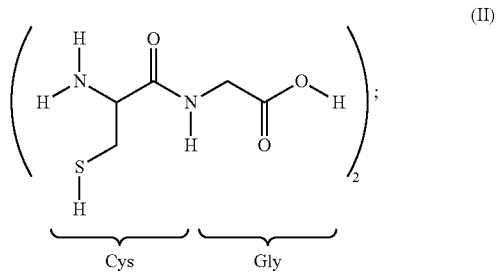

III) a tocopherol or a derivative thereof; and

IV) a mixture thereof.